US011670585B1

(12) United States Patent
Jain

(10) Patent No.: US 11,670,585 B1
(45) Date of Patent: Jun. 6, 2023

(54) POWER DISTRIBUTION FOR ACTIVE-ON-ACTIVE DIE STACK WITH REDUCED RESISTANCE

(71) Applicant: XILINX, INC., San Jose, CA (US)

(72) Inventor: Praful Jain, San Jose, CA (US)

(73) Assignee: XILINX, INC., San Jose, CA (US)

( * ) Notice: Subject to any disclaimer, the term of this patent is extended or adjusted under 35 U.S.C. 154(b) by 75 days.

(21) Appl. No.: 17/354,942

(22) Filed: Jun. 22, 2021

Related U.S. Application Data

(63) Continuation of application No. 15/902,703, filed on Feb. 22, 2018, now Pat. No. 11,041,211.

(51) Int. Cl.
*H01L 23/48* (2006.01)
*H01L 23/522* (2006.01)
(Continued)

(52) U.S. Cl.
CPC .......... *H01L 23/5228* (2013.01); *C07K 16/32* (2013.01); *C12Q 1/6886* (2013.01); *G01N 33/57434* (2013.01); *H01L 23/481* (2013.01); *H01L 23/5222* (2013.01); *H01L 23/5226* (2013.01); *H01L 23/5286* (2013.01); *H01L 25/0657* (2013.01); *H01L 25/50* (2013.01); *C07K 2317/565* (2013.01);
(Continued)

(58) Field of Classification Search
CPC ............ C12Q 1/6886; C12Q 2600/106; C12Q 2600/158; C12Q 2600/112; C12Q 2600/118; G01N 33/57434; G01N 2800/52; G01N 2333/4703; H01L 23/5286; H01L 23/5226; H01L 25/50; H01L 23/5228; H01L 23/481; H01L 25/0657; H01L 23/5222; H01L 2224/0557; H01L 2225/06541; H01L 2225/06544; H01L 2224/0401; H01L 2225/06548; C07K 16/32; C07K 2317/565
USPC ........................................................ 257/777
See application file for complete search history.

(56) References Cited

U.S. PATENT DOCUMENTS 5,097,440 A  3/1992 Konishi et al.
6,737,925 B1  5/2004 Logue et al.
(Continued)

FOREIGN PATENT DOCUMENTS

CN  1925147 A  3/2007
EP  3229270 A1  10/2017
(Continued)

*Primary Examiner* — Hrayr A Sayadian
(74) *Attorney, Agent, or Firm* — Patterson + Sheridan, LLP

(57) ABSTRACT

Active-on-active microelectronic devices are described. For example, a first die is on a second die with a bottom surface of a first substrate facing a top surface of a second substrate, respectively, to provide a die stack. The first and second dies each have metal layers in ILD layers to provide a first stack structure and a second stack structure, respectively. The first stack structure is interconnected to an upper end of a TSV of the first die. A metal layer of the second stack structure near a bottom surface of the first substrate is interconnected to a lower end of the TSV. A power distribution network layer of the second stack structure is located between lower and upper layers of the metal layers thereof. A transistor located at least in part in the second substrate is interconnected to the power distribution network layer to receive supply voltage or ground.

20 Claims, 9 Drawing Sheets

(51) Int. Cl.
  *H01L 25/065* (2023.01)
  *H01L 25/00* (2006.01)
  *H01L 23/528* (2006.01)
  *C07K 16/32* (2006.01)
  *C12Q 1/6886* (2018.01)
  *G01N 33/574* (2006.01)

(52) U.S. Cl.
  CPC .. *C12Q 2600/106* (2013.01); *C12Q 2600/112* (2013.01); *C12Q 2600/118* (2013.01); *C12Q 2600/158* (2013.01); *G01N 2333/4703* (2013.01); *G01N 2800/52* (2013.01); *H01L 2224/0401* (2013.01); *H01L 2224/0557* (2013.01); *H01L 2225/06541* (2013.01); *H01L 2225/06544* (2013.01); *H01L 2225/06548* (2013.01)

(56) References Cited

U.S. PATENT DOCUMENTS

| | | | |
|---|---|---|---|
| 7,312,625 B1 | 12/2007 | Paak et al. |
| 7,893,712 B1 | 2/2011 | Tan et al. |
| 8,008,121 B2 | 8/2011 | Choi et al. |
| 8,313,982 B2 | 11/2012 | Dunne et al. |
| 8,674,496 B2 | 3/2014 | Lin et al. |
| 8,759,959 B2 | 6/2014 | Yim et al. |
| 8,803,332 B2 | 8/2014 | Lee et al. |
| 8,890,730 B2 | 11/2014 | Lowney et al. |
| 8,975,711 B2 | 3/2015 | Otremba et al. |
| 8,982,581 B2 | 3/2015 | Karp et al. |
| 9,184,623 B1 | 11/2015 | Cical et al. |
| 9,419,624 B2 | 8/2016 | Lesea |
| 9,559,040 B2 | 1/2017 | Batra et al. |
| 9,577,615 B1 | 2/2017 | Ganusov et al. |
| 9,754,923 B1 | 9/2017 | Xie et al. |
| 9,768,105 B2 | 9/2017 | Lii et al. |
| 10,032,707 B2 | 7/2018 | Lai et al. |
| 2004/0056355 A1 | 3/2004 | Minami et al. |
| 2006/0197228 A1 | 9/2006 | Daubenspeck et al. |
| 2008/0320254 A1 | 12/2008 | Wingard et al. |
| 2010/0225002 A1 | 9/2010 | Law et al. |
| 2011/0002489 A1 | 1/2011 | Schefer |
| 2011/0084314 A1* | 4/2011 | Or-Bach ........... H01L 27/10897 257/209 |
| 2011/0215478 A1 | 9/2011 | Yamamichi et al. |
| 2011/0278732 A1 | 11/2011 | Yu et al. |
| 2012/0032326 A1 | 2/2012 | Kim et al. |
| 2013/0073878 A1 | 3/2013 | Jayasimha et al. |
| 2013/0221499 A1 | 8/2013 | Karikalan et al. |
| 2014/0117453 A1 | 5/2014 | Lu |
| 2014/0325247 A1 | 10/2014 | Sodhi et al. |
| 2015/0187733 A1 | 7/2015 | Batra et al. |
| 2015/0348962 A1 | 12/2015 | Chao et al. |
| 2015/0371971 A1 | 12/2015 | Yokoyama et al. |
| 2016/0064364 A1 | 3/2016 | Shin et al. |
| 2016/0141274 A1 | 5/2016 | Or-Bach et al. |
| 2016/0211241 A1 | 7/2016 | Law et al. |
| 2016/0225679 A1 | 8/2016 | Kannan et al. |
| 2018/0145030 A1 | 5/2018 | Beyne et al. |
| 2019/0198443 A1 | 6/2019 | Nakano et al. |

FOREIGN PATENT DOCUMENTS

| | | |
|---|---|---|
| EP | 3324436 A1 | 5/2018 |
| JP | 2007067216 A | 3/2007 |
| JP | 2011228419 A | 11/2011 |
| JP | 2014057065 A | 3/2014 |

* cited by examiner

POWER DISTRIBUTION FOR ACTIVE-ON-ACTIVE DIE STACK WITH REDUCED RESISTANCE

FIELD OF THE INVENTION

The following description relates to integrated circuit devices ("ICs"). More particularly, the following description relates to power distribution for an active-on-active die stack with reduced resistance for reducing current-resistance ("IR") loss in a microelectronic device.

BACKGROUND

Integrated circuits have become more "dense" over time, i.e., more logic features have been implemented in an IC of a given size. However, to further increase circuit density, integrated circuit dies are stacked on upon one another to form a die stack, such as for a "3D" IC. However, there are limitations due to voltage drop in such a die stack. For example, one possible limitation may be voltage drop along power rails, namely power and/or ground conductive paths, of a die stack.

SUMMARY

An apparatus relates generally to an active-on-active microelectronic device. In such an apparatus, a first die has a first substrate with a through-substrate via extending between a top surface and a bottom surface of the first substrate. A second die has a second substrate with a top surface and a bottom surface. The first die is on the second die with the bottom surface of the first substrate facing the top surface of the second substrate to provide a die stack. The first die and the second die each have a plurality of metal layers formed in a plurality of inter-level dielectric layers to provide a first stack structure and a second stack structure, respectively, for electrical conductivity. The first stack structure is interconnected to an upper end of the through-substrate via for electrical conductivity. A metal layer of the second stack structure near the bottom surface of the first substrate is interconnected for electrical conductivity to a lower end of the through-substrate via. A power distribution network layer of the second stack structure is located between lower layers and upper layers of the plurality of metal layers thereof. A first transistor and a second transistor are respectively located at least in part in the first substrate and the second substrate. The second transistor is interconnected to the power distribution network layer to receive at least one of a supply voltage or a ground.

A method relates generally to forming an active-on-active microelectronic device. In such a method, a first die is obtained. The first die has a first substrate with a through-substrate via extending between a top surface and a bottom surface of the first substrate. A second die having a second substrate with a top surface and a bottom surface is obtained. The first die is interconnected on the second die with the bottom surface of the first substrate facing the top surface of the second substrate to provide a die stack. The first die and the second die each have a plurality of metal layers formed in a plurality of inter-level dielectric layers to provide a first stack structure and a second stack structure, respectively, for electrical conductivity. The first stack structure is interconnected to an upper end of the through-substrate via for electrical conductivity. A metal layer of the second stack structure near the bottom surface of the first substrate is connected for electrical conductivity to a lower end of the through-substrate via as part of the interconnecting of the first and second dies. A power distribution network layer of the second stack structure is located between lower layers and upper layers of the plurality of metal layers thereof. A first transistor and a second transistor are respectively located at least in part in the first substrate and the second substrate. The second transistor is interconnected to the power distribution network layer to receive at least one of a supply voltage or a ground.

Other features will be recognized from consideration of the Detailed Description and Claims, which follow.

BRIEF DESCRIPTION OF THE DRAWINGS

Accompanying drawings show exemplary apparatus(es) and/or method(s). However, the accompanying drawings should not be taken to limit the scope of the claims, but are for explanation and understanding only.

FIG. 2-1 is a block diagram depicting a side view of an exemplary portion of a microelectronic device having a die stack.

FIG. 2-2 is a block diagram depicting a side view of an exemplary portion of another microelectronic device having another die stack.

FIG. 3-1 is a block diagram depicting a cross-sectional view of an exemplary portion of a semiconductor die at a lower metalization level.

FIG. 3-2 is a block diagram depicting a cross-sectional view of an exemplary portion of a semiconductor die at an upper metalization level.

FIG. 3-3 is a block diagram depicting a cross-sectional view of an exemplary portion of a semiconductor die at an intermediate power distribution network level.

FIG. 4-1 is a block diagram depicting a side view of an exemplary portion of yet another microelectronic device having a die stack as in FIG. 2-1.

FIG. 4-2 is a block diagram depicting a side view of an exemplary portion of still yet another microelectronic device having yet another die stack.

DETAILED DESCRIPTION

Figure 1:
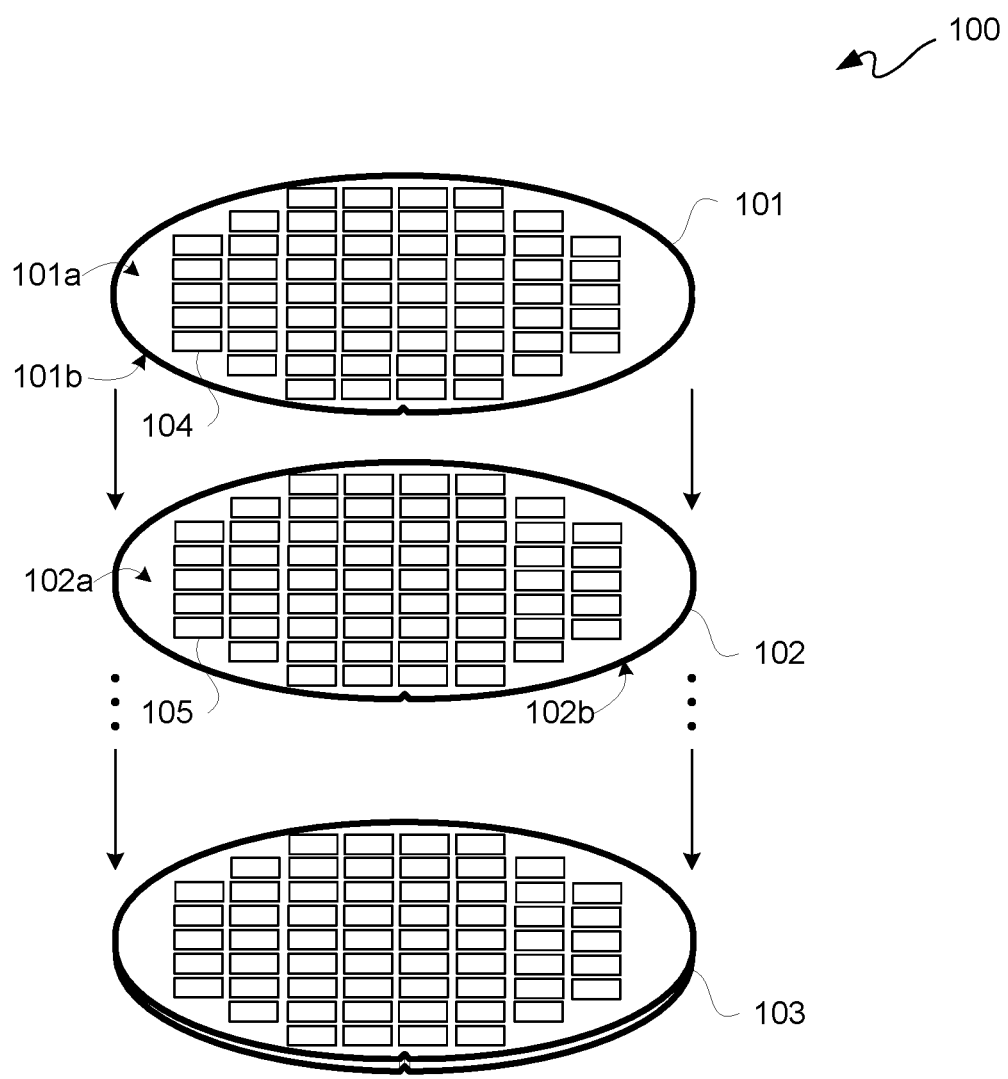
FIG. 1 is a perspective diagram depicting a top-down and side view of an exemplary in-process wafer stack for wafer-level processing ("WLP").

In the following description, numerous specific details are set forth to provide a more thorough description of the specific examples described herein. It should be apparent, however, to one skilled in the art, that one or more other examples and/or variations of these examples may be practiced without all the specific details given below. In other instances, well known features have not been described in detail so as not to obscure the description of the examples herein. For ease of illustration, the same number labels are used in different diagrams to refer to the same items; however, in alternative examples the items may be different.

Exemplary apparatus(es) and/or method(s) are described herein. It should be understood that the word "exemplary" is used herein to mean "serving as an example, instance, or illustration." Any example or feature described herein as "exemplary" is not necessarily to be construed as preferred or advantageous over other examples or features.

Before describing the examples illustratively depicted in the several figures, a general introduction is provided to further understanding. As traditional "2D" scaling becomes more challenging with smaller and smaller semiconductor processing nodes, stacking separate dies, such as semiconductor substrate dies or semiconductor dies, one on another using through-substrate vias ("TSVs") becomes a more appealing approach to increase circuit density. Along those lines, an active-on-active die stack may be used as or as part of a die stack.

Because of the structure of a die stack, it does not make sense to continue to be bound by configuration of a 2D die. In other words, a die stack need not be made up of a stack of conventional 2D dies.

Voltage or current-resistance ("IR") drops increase, in some instances doubling, with each semiconductor processing node advancement. A steep increase in IR drop on voltage and ground power rails in sub-20 nanometer semiconductor process nodes has been observed. This means that using a conventional 2D die for stacking, such as to provide an active-on-active die stack for example, may cause significant IR drops. An accumulation of IR drops reduces the available voltage across components, such as transistors for example. If a supply voltage or supply power is increased to address such accumulation of IR drops, power consumption may increase.

However, to lower power consumption in microelectronic devices, supply voltage downward scaling has been used. A reduction in supply voltage combined with additional IR drop has made meeting performance targets substantially more difficult.

TSVs, as well as corresponding chimney-like stack structures, namely "chimneys" or "chimney stacks," used to carry power and ground current in such die stacks have a cumulative IR drop, which can be more substantial than IR drop in a conventional non-stacked 2D die. In a conventional non-stacked 2D die configuration, power and ground distribution originates from the uppermost conductive layer and propagates down metalization levels to a substrate. In a die stack of conventional 2D dies, power and ground distribution may originate from a back-side of a substrate up through TSVs and chimney metalization levels to the uppermost metalization level and then back down through such metalization levels to a substrate.

Conventional place and route ("PnR") cells or blocks for chimney construction reduce IR drop by having more conductive vias between metal layers. Additionally, by having more chimneys, impact of IR drops or losses can be reduced. However, these configurations use more area which increases cost per die.

In contrast to power and ground distribution in such a conventional die stack, a lower resistance path for power and ground distribution is described below in additional detail. As described below, a chimney interim buss path is provided to bypass chimney metalization levels to reduce IR drop. Such a chimney interim buss path may be provided with a power and ground distribution network ("PDN") metalization layer. An "early off-ramp" buss from a chimney for conducting current for a power or a ground path reduces IR drop. Such an "early off-ramp" is provided with an intermediate metalization level being formed thicker than a conventional intermediate metalization level. By providing a thicker intermediate metalization level for power and ground distribution, namely thick traces for power and ground bussing, IR drop may be reduced as compared with conventional power and ground routing in a die stack. IR drop can be reduced by at least 20 percent without having to increase area and thus increase cost per die.

With the above general understanding borne in mind, various configurations for die stacks are generally described below.

FIG. 1 is a perspective diagram of a top-down and side view depicting an exemplary in-process wafer stack 100 for wafer-level processing ("WLP"). A top wafer 101 and a bottom wafer 102 may be coupled to one another. For example, a Cu/Sn microbump transient liquid phase ("TLP") bonding technology may be used for bonding or otherwise interconnecting one die to another at a die-to-die level, a wafer-to-wafer level, or a die-to-wafer level, for electrical conductivity as well as mechanical coupling. However, other types of interconnecting one die to another may be used.

Interconnect layers may be on an upper or lower side or both upper and lower sides of a die of a 3D die stack. A lower surface 101b and an upper surface 102a, respectively of wafers 101 and 102, may face one another after such coupling with die-to-die interconnects interconnecting corresponding dies of a die stack for electrical conductivity. Along those lines, a semiconductor die ("active die") 104 of top wafer 101 may be coupled to a corresponding active die 105 of bottom wafer 102 to form a stacked wafer 103 of stacked dies or die stacks.

Each of semiconductor dies 104 and 105 may include a substrate of a semiconductor material such as silicon (Si), gallium arsenide (GaAs), a silicon carbon (SiC), germanium (Ge), $Si_{1-x}Ge_x$, or the like. Furthermore, any microelectronic component having a die stack with a substrate that includes one or more through-substrate via structures and two or more active dies may be used. An active die may be distinguished from a passive die, as an active die includes a transistor, and a passive die does not have a transistor. Active-on-active die stacks are described below.

As used herein with respect to wafers, dies, and substrates, among other structures, terms are used such as an "upper surface" and a "lower surface" to indicate features extending generally in "horizontal" or other lateral directions and generally parallel to each other at a thickness. Use of terms such as "horizontal", "upper" and "lower" or other directional terms is made with respect to the reference frame of the figures and/or orientations during processing and is not meant to be limiting with respect to potential alternative orientations, such as in further assemblies or as used in various systems.

Along those lines, in processing a wafer 101 or 102, an upper surface 101a or 102a, respectively, may generally be associated with what is referred to as a "front-side" of an in-process wafer, and lower surface 101b or 102b, respectively, may generally be associated with what is referred to as a "back-side" of an in-process wafer. Along those lines, a front-side of an in-process wafer may be used for forming what is referred to as front-end-of-line ("FEOL") structures, and a back-side of an in-process wafer may be used for forming back-end-of-line ("BEOL") structures. Generally, FEOL structures may include shallow trench isolations ("STI"), transistor gates, transistor source/drain regions, transistor gate dielectrics, a contact etch stop layer ("CESL"), a pre-metallization dielectric or pre-metal dielectric ("PMD"), and contact plugs, among other FEOL structures. A PMD may be composed of one or more layers. Generally, BEOL structures may include one or more inter-level dielectrics ("ILDs") and one or more levels of metallization ("M"). In the following examples, a number of ILDs are illustratively depicted; however, in other configurations there may be fewer or more ILDs than those illustratively depicted. Furthermore, each ILD may be composed of one or more dielectric layers. In the following examples, a number of metallization levels or metal layers are illustratively depicted; however, in other configurations there may be fewer or more levels of metallization than those illustratively depicted. Additionally, metal from a metallization level may extend through one or more ILDs, in the form of conductive vias as is known. Furthermore, each level of metallization may be composed of one or more metal layers.

A passivation level may be formed on a last or uppermost metallization layer or level. Such passivation level may include one or more dielectric layers, and further may include an anti-reflective coating ("ARC"). A passivation layer may be formed of one or more dielectric layers, such as a polymer layer. For example, passivation layer may be a benzocyclobutene ("BCB") layer or a combination of a silicon nitride layer and a BCB layer. In some die stack applications, a passivation layer may be referred to as an inter-die layer.

A metal layer, such as a copper, copper alloy, or other metal, may be formed on a passivation layer and on lower end contact surfaces of uppermost via conductors. This metal layer may be an RDL metal layer. Balls or bumps may be respectively formed on bonding pads, where such pads may be formed on or as part of such a metal layer. Balls may be formed of a bonding material, such as solder or other eutectic bonding material. Balls may be microbumps, C4 bumps, ball grid array ("BGA") balls, or some other die interconnect structures. In some applications, the uppermost metal layer may be referred to as a landing pad layer or landing pad.

Furthermore, a redistribution layer ("RDL") may be formed on such passivation level. Conventionally, an RDL may include: a dielectric layer, such as a polyimide layer for example; another metal layer on such dielectric layer and connected to a bond pad of a metal layer of a last metallization level; and another dielectric layer, such as another polyimide layer for example, over such RDL metal layer while leaving a portion thereof exposed to provide another bond pad. A terminal opening may expose such other bond pad of such RDL metal layer. Thereafter, a solder bump or wire bond may be conventionally coupled to such bond pad.

As part of a FEOL or BEOL structure formation, a plurality of via structures may extend within openings formed in a substrate which extend into substrate. Via structures may be generally in the form of any solid of any shape formed by filling or plating an opening or hole formed in a substrate. Examples of such solid shapes generally include cylindrical, conical, frustoconical, rectangular prismatic, cubic, or the like.

Conventionally, through-substrate via structures or TSVs may extend from an upper surface of a substrate down to or toward a lower surface of a substrate, namely a front-side TSV is initially formed by etching from a front-side of a substrate and then plating or otherwise depositing material into such etch hole in such substrate. Along those lines, after a back-side reveal to expose bottoms of such TSVs, TSVs may extend between upper and lower surfaces of a substrate, as effectively thickness of a substrate may be thinned so as to reveal lower end surfaces of TSVs. However, a TSV may have a back-side via structure. Fabrication of a back-side TSV is generally referred to as a "via last approach," and accordingly fabrication of a front-side TSV is generally referred to as a "via first approach." Furthermore, a "via middle approach" may be used. A "via middle approach" is likewise a front-side approach to via formation, but referred to as "middle" as vias are made after FEOL operations, but generally before BEOL operations. The following description is generally equally applicable to front-side or back-side TSVs of any or all of a via first, last or middle approach to formation.

TSVs may each include an upper end contact surface which may be level with an upper surface of a substrate and a lower end contact surface which may be level with a lower surface of such a substrate, such as after a back-side reveal. End surfaces may be used to interconnect TSV with other internal or external components, as described below in additional detail.

For example, an upper end contact surface of a via conductor may be interconnected to a first metalization level ("M1") through a respective contact pad. Contact pads may be formed in respective openings formed in a PMD to which M1 extends. However, in other configurations, one or more via conductors may extend to one or more other higher levels of metallization through one or more ILDs.

More recently, TSVs have been used to provide what is referred to as three-dimensional ("3D") ICs or "3D ICs." Generally, attaching one die to another with TSVs as conductive pathways through a substrate may be performed at a bond pad level or an on-chip electrical wiring level; however, wafer-to-wafer bonding may be used. Semiconductor dies, such as semiconductor dies 104 and 105, may be respectively diced from wafers 101 and 102 into single dies. Such single dies may be bonded to one another or bonded to a circuit platform. Interposers, package substrates, and printed circuit boards are examples of circuit platforms.

3D wafer-level packaging ("3D-WLP") may be used for interconnecting two or more dies, one or more dies to an interposer, or any combination thereof, where interconnects thereof may use TSVs. Optionally, dies may be interconnected die-to-die ("D2D") or chip-to-chip ("C2C"), where interconnects thereof may use TSVs. Further, optionally, dies may be interconnected die-to-wafer ("D2 W") or chip-to-wafer ("C2 W"), where interconnects thereof may use TSVs. Accordingly, any of a variety of die stacking or chip stacking approaches may be used to provide a 3D stacked IC ("3D-SIC" or "3D-IC").

For purposes of clarity by way of example and not limitation, it shall be assumed that die level packaging with D2D die stacks are used having at least two active dies in a die stack. As WLP for die-to-die stacking is presently not the convention for commercial production of a 3D die stack, diced die-to-die stacking is described below in additional detail. However, other configurations may be used in accordance with the description herein, including without limitation WLP. Furthermore, many of the above described details regarding formation of semiconductor dies are not repeated below for purposes of clarity and not limitation.

Figures 1, 2:
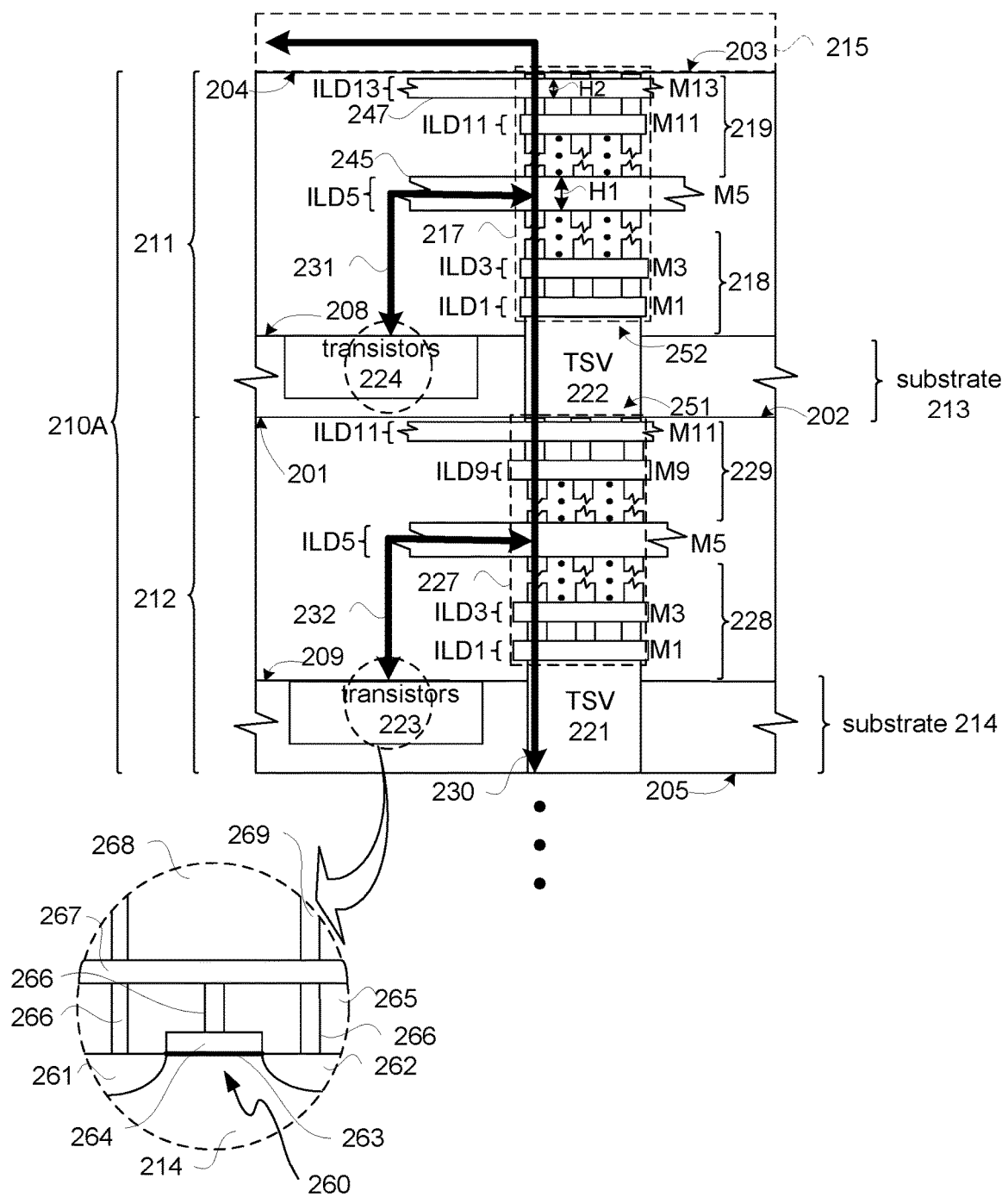
Figure 2:
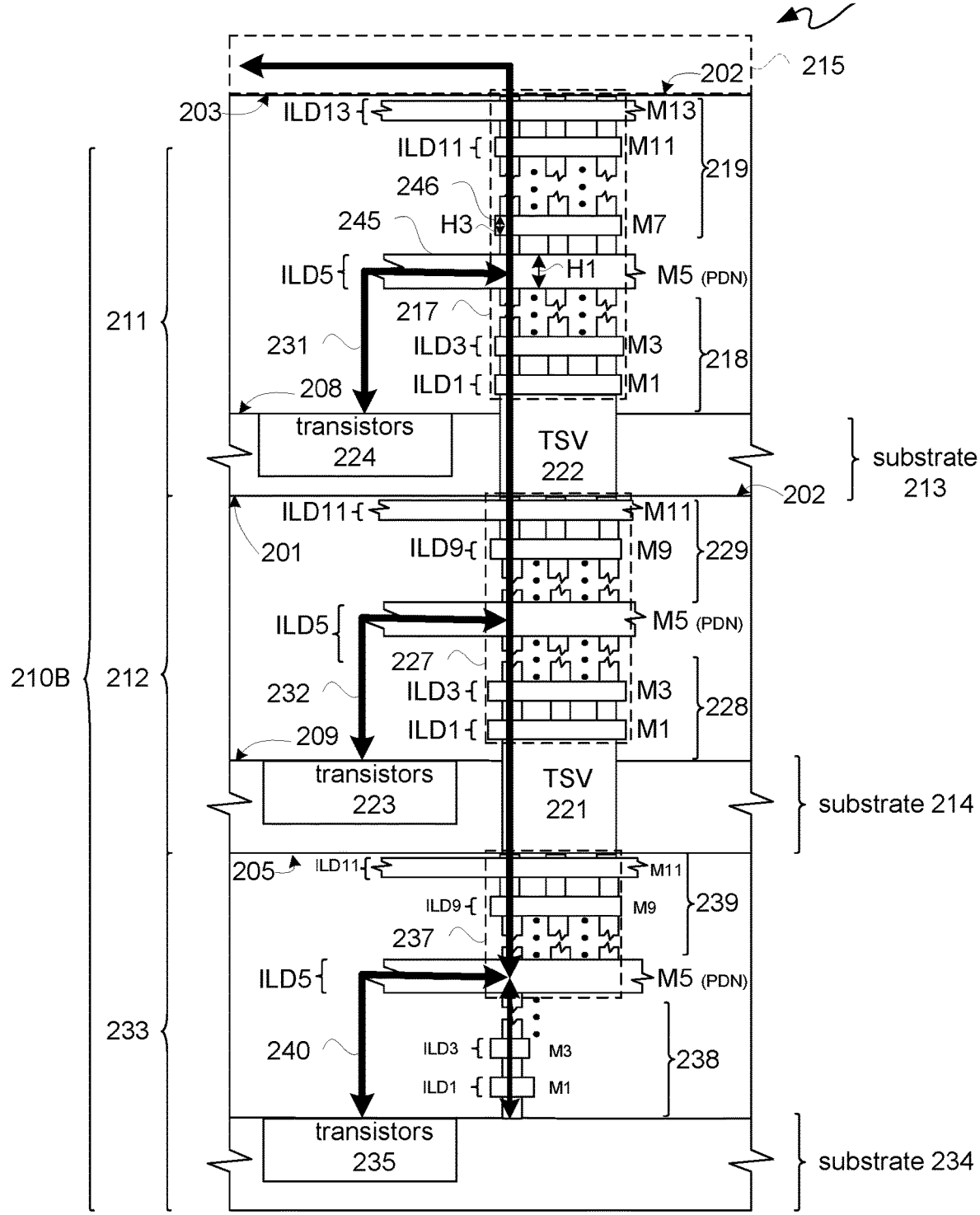

FIG. 2-1 is a block diagram depicting a side view of an exemplary portion of a microelectronic device 200A having a die stack 210A. Die stack 210A includes an upper semiconductor die 211 and a lower semiconductor die 212 coupled to one another. A back-side surface 201 of upper semiconductor die 211 is coupled to a front-side surface 202 of lower semiconductor die 212, namely a lower surface 201 and an upper surface 202 face one another.

Upper semiconductor die 211 includes a substrate 213 having a TSV 222. Even though only one TSV 222 is illustratively depicted for purposes of clarity, substrate 213 may include more than one TSV. TSV 222 extends between upper surface 208 of substrate 213 and back-side surface 201 of substrate 213. In this example for purposes of clarity and not limitation, back-side surface 201 is of a substrate 213 of upper semiconductor die 211. However, in another example, a back-side surface of a semiconductor die may be a surface of a back-side RDL or other one or more layers formed on such back-side surface 201 of substrate 213. Moreover, in this example, TSV 222 extends above upper surface 208, such as with use of a PMD layer used to provide a form for a portion of TSV 222. This is merely for convenience for showing TSV 222 is interconnected to a metal layer M1. However, as described below in additional detail, a metal layer M1 may be used to form conductive vias, which may be interconnects to a TSV 222.

Upper semiconductor die 211 may include circuitry components forming circuits, where such circuitry components may include one or more transistors 224 as well as other circuitry components, as generally depicted for purposes of clarity and not limitation. In an example, gates and gate dielectrics (not particularly depicted for purposes of clarity and not limitation) may be located above an upper surface 208 of substrate 213.

Upper semiconductor die 211 includes a "chimney" or "chimney stack" 217. Even though only one "chimney" or "chimney stack" is illustratively depicted for purposes of clarity, upper semiconductor die 211 or another semiconductor die described herein may include more than one "chimney." Chimney 217 is formed with multiple metalization and ILD levels. In this example, non-chimney portions of lower metalization and ILD levels 218 of semiconductor die 211 are generally used for interconnection between components, such as for example circuitry components which may include one or more transistors 224. In this example, non-chimney portions of upper metalization and ILD levels 219 of semiconductor die 211 are generally used for interconnection between semiconductor die 211 and circuit platform 215, as well as "global" on-die routing, such as clock and other signals.

For this example, there are 13 metalization levels M1 through M13, and a corresponding 13 ILD levels ILD1 through ILD13. In this example, a power distribution network ("PDN") metal layer M5 is thicker or taller than all other metalization levels of metalization levels M1 through M13. Such a PDN layer M5 is between upper and lower metalization levels, and generally may be a first metalization level above a last routing metalization level for direct interconnect routing of repeated cells of circuitry, sometimes referred to as a first metalization level above a last "standard cell" metal routing layer. In this example, a PDN layer M5 is at least twice as tall as an immediately neighboring upper metal layer with respect to thickness of horizontal traces respectively thereof. In this example, height H1 of a horizontal trace 245 of PDN layer M5 is at least twice height H2 of a chimney stack portion horizontal trace 247 of metalization layer M13. More generally, in an example, a PDN layer M5 was configured to have a lowered resistivity, where in such example a resistivity of less than 30 ohms for a length of at least 30 microns for a horizontal trace thereof, such as horizontal trace 245, was observed. By horizontal trace, it is generally meant a conductive line formed in a trench defined in an ILD, where such conductive line follows such trench, which may be convention may have horizontal extent with respect to a plane of an ILD thereof. Without the aforementioned enhancements, total resistance from an uppermost metal layer in a BEOL stack down to transistor regions in a substrate in "2D" IC may be 120 ohms in a complex FPGA. Though this number may be significantly smaller for conventional placed and routed ASICs, such number is still a burden with respect to voltage drop on one or more power rails.

Even though a 13-level BEOL chimney is illustratively depicted fewer or more metalization and corresponding ILD levels may be used in other examples in accordance with the description herein. The uppermost metal layer or metalization level M13 associated with an upper surface 203 of semiconductor die 211, which may include one or more layers of material, may be interconnected for electrical conductivity to conductive contacts (not shown for purposes of clarity and not limitation) along surface 204 of circuit platform 215, and thus such metalization level M13 in this example may be in part a power and ground distribution layer.

In a region of chimney 217, portions of lower and upper metalization and ILD levels 218 and 219 are used to provide a low resistivity path by increasing conductive via density in such chimney region for purposes of metalization-level-to-metalization-level electrical conductivity. Between lower and upper metalization and ILD levels 218 and 219 is a PDN metal layer M5 and corresponding ILD level ILD5. Likewise, portions of PDN metal layer M5 with ILD level ILD5 in a region of chimney 217 are used to provide a more localized power and ground routing to one or more circuitry components, where such circuitry components may include one or more of transistors 223 and 224, respectively. Such localized power and ground routing from a PDN metal layer M5 may be used in order to have a lowered resistivity path by increasing conductive via density in a chimney region associated with such PDN metal layer M5 in comparison to a upper metal layer with respect thereto for purposes of metalization-level-to-metalization-level electrical conductivity. Such routing is more local than having power and ground routing go from the uppermost metal layer of an IC down to one or more transistors thereof. Additionally, an intermediate metalization level used to provide PDN metal layer, such as PDN metal layer M5 for example, may include, including without limitation exclusively include, in-die power and ground routed bussing with respect to such metalization layer.

Because a front-side surface conventionally has many more opportunities for electrical interconnects than a back-side surface, a front-side surface 203, namely upper surface 203, may be coupled to a lower surface 204 of a printed circuit board, interposer substrate, RDL stack, package substrate, or other circuit platform 215 to couple die stack 210A to such a circuit platform 215. Circuit platform 215 may be used to provide off-die power and ground routed bussing, as generally indicated with arrow 230.

Lower semiconductor die 212 includes a substrate 214 having a TSV 221. Even though only one TSV 221 is illustratively depicted for purposes of clarity, substrate 214 may include more than one TSV. TSV 221 extends between upper surface 209 and lower surface 205 of substrate 214. In this example for purposes of clarity and not limitation, lower surface 205 of a substrate 214 is a back-side surface 205 of lower semiconductor die 212. However, in another example, a back-side surface of a semiconductor die may be a surface of a back-side RDL or other one or more layers formed on such back-side surface 205 of substrate 214.

Lower semiconductor die 212 may include circuitry components, such as may include one or more transistors 223, as well as other circuitry components, as generally depicted for purposes of clarity and not limitation. In an example, gates and gate dielectrics may be located above an upper surface 209 of substrate 214.

An enlarged view of a portion of a MOSFET transistor 260 of transistors 223 or transistors 224, is depicted for purposes of clarity by way of example and not limitation. A transistor 260 of transistors 223 and a transistor 260 of transistors 224 may each be formed at least in part in substrates 214 and 213, respectively. In another example, another type of transistor may be formed. Each transistor 260 may include a source region 261 and a drain region 262 formed in substrate 214. A gate dielectric 263 may be formed on substrate 214, and a gate electrode 264 may be formed on gate dielectric 263. A conductive layer, such as an M1 for example, may be used to form conductive vias 266 for conductivity to source region 261, gate electrode 264, and/or drain region 262. Conductive vias 266 may be formed in a dielectric layer 265. Another or a same metal layer used to form conductive vias 266 may be used to form horizontal conductive lines, such as conductive line 267 for example, which may be interconnected for electrical conductivity to one or more of conductive vias 266. Another dielectric layer 268 may be formed above conductive line 267 for another metal layer to provide conductive vias 269. One or more of conductive vias 269 may be interconnected for electrical conductivity to one or more conductive lines, such as conductive line 267 for example. Moreover, one or more of conductive vias 266 may be directly or indirectly interconnected to a power distribution network ("PDN") metal layer M5, as described below in additional detail. Along those lines, one of conductive vias 266 may be used to provide either a power supply voltage or a ground voltage to source region 261, drain region 262, and/or gate electrode 264 of transistor 260 for operation of same. Likewise, another one of conductive vias 266 may be used to provide either a power supply voltage or a ground voltage to another of source region 261, drain region 262, and/or gate electrode 264 of transistor 260 for operation of same. Though only a single transistor 260 of transistors 223 and 224 is depicted for purposes of clarity, more than one transistor 260 of transistors 223 and 224 may likewise be provided with power and/or ground.

Lower semiconductor die 212 includes a "chimney" or "chimney stack" 227. Even though only one "chimney" is illustratively depicted for purposes of clarity, lower semiconductor die 212 may include more than one "chimney." Chimney 227 is formed with multiple metalization and ILD levels. The uppermost metalization level, such as M11 for example, of semiconductor die 212 may be interconnected for electrical conductivity to a lower end or lower end surface 251 of TSV 222. The lowermost metalization layer, such as M1 for example, of semiconductor die 211 may be interconnected for electrical conductivity to an upper end or upper end surface 252 of TSV 222. By having metalization layer M1 as the lowermost metalization layer of lower semiconductor die 212 means a metal layer for TSV 221, which may include a PMD layer for example, is not included as part of a BEOL stack.

In this example, non-chimney portions of lower metalization and ILD levels 228 of semiconductor die 212 are generally used for interconnection or routing between components, such as for example transistors 223. In this example, non-chimney portions of upper metalization and ILD levels 229 of semiconductor die 212 are generally used for interconnection or routing between semiconductor die 212 and semiconductor die 211, as well as "global" on-die routing, such as clock and other signals. For this example, there are 11 metalization levels M1 through M11, and a corresponding 11 ILD levels ILD1 through ILD11. A power distribution network ("PDN") metal layer M5 may be thicker or taller than all other metalization levels of metalization levels M1 through M11 same as described with reference to PDN layer M5. In this example, height H1 of a horizontal trace 245 of PDN layer M5 is at least twice height H3 of a chimney stack portion horizontal trace 246 of metalization layer M7. Again, a PDN metal layer M5 is configured to have a lowered resistivity. In an example, a PDN metal layer M5 having a resistivity of less than 30 ohms for a length of at least 30 microns has been observed.

Even though a 11-level BEOL chimney stack structure is illustratively depicted, fewer or more metalization and corresponding ILD levels may be used in other examples in accordance with the description herein. Moreover, even though in this example different semiconductor dies 211 and 212 with respect to numbers of levels of BEOL structures are used, in another example semiconductor dies 211 and 212 may have a same number of levels of BEOL structures.

The uppermost metal layer, such as in this example metalization level M11, of semiconductor die 212 may include one or more layers of conductor material and one or more barrier layers. Again, such uppermost metal layer may be interconnected for electrical conductivity to conductive contacts for interconnection to a lower side or lower end surface 251 of TSV 222, which may be along surface 201 of upper semiconductor die 211.

In a region of chimney 227, lower and upper metalization and ILD levels 228 and 229 are used to provide a low resistivity path by increasing conductive via density in such chimney region for purposes of metalization-level-to-metalization-level electrical conductivity. Between lower and upper metalization and ILD levels 228 and 229 is a PDN metal layer M5 and corresponding ILD level ILD5. Likewise, in a region of chimney 227 PDN metal layer M5 with ILD level ILD5 are used to provide a low vertical resistivity path by increasing conductive via density in such chimney region for purposes of metalization-level-to-metalization-level electrical conductivity. Again, the uppermost metal layer, such as metalization level M11 in this example, which may include one or more layers of material, may be interconnected for electrical conductivity to a lower end of TSV 222.

Optionally or additionally, a back-side surface 205, namely a lower surface, of substrate 214 may be coupled to another semiconductor die. Along those lines, TSVs and chimneys respectively of semiconductor dies of a die stack may be vertically aligned with respect to one another to provide a low resistance path for conduction of current in either an upward or downward direction within such a die stack as applicable. Such a low resistance conductive path may be used for providing a power supply voltage into die stack 210A or a path to ground out of die stack 210A, as generally indicated with arrow 230. Intra-die power or ground routing using lower metalization levels 218 and 228 respectively from metalization levels M5 respectively thereof may be provided, as generally respectively indicated with arrows 231 and 232. Such intra-die power and ground routing may be used for operation of transistors 224 and 223.

In this example, chimney 217, TSV 222, chimney 227, and TSV 221 are all vertically aligned with one another to provide a low vertical resistance path to a next semiconductor die in die stack 210A. If, however, only semiconductor dies 211 and 212 are used for through die low resistance routing in a die stack 210A, a last (lowermost for the orientation in FIG. 2-1) semiconductor die 233 in a die stack may have a portion of chimney 227 and all of a corresponding TSV omitted, as illustratively depicted in BEOL lower layers 238 of semiconductor die 233 of a semiconductor die stack 210B of FIG. 2-2.

FIG. 2-2 is a block diagram depicting a side view of an exemplary portion of a microelectronic device 200B having a die stack 210B. Die stack 210B includes semiconductor dies 211 and 212, as previously described, as well as a third lower semiconductor die 233. For purposes of clarity the previous description of semiconductor dies 211 and 212 is not repeated for description of microelectronic device 200B, as much of microelectronic device 200B is the same as microelectronic device 200A of FIG. 2-1. Accordingly, for purposes of clarity generally only the differences are described.

The lowermost semiconductor die 233 of die stack 210B includes a partial chimney 237. Partial chimney 237 includes upper metalization and ILD levels 239 and a PDN metalization level M5 and corresponding ILD level ILD5. However, while lower metalization and ILD levels 238 are present below PDN metalization level M5 and corresponding ILD level ILD5, such lower levels 238 are not used to provide a partial chimney in semiconductor die 233. However, such lower levels 238 may be used to provide conventional power and ground routing to substrate 234 of semiconductor die 233, such as for transistors 235, as generally indicated, thereof. While providing additional area for routing, current carrying capacity for power and ground of conventional routing in lower levels 238 is less than in a chimney, resulting in higher resistances than in a chimney.

With simultaneous reference to FIGS. 2-1 and 2-2, microelectronic devices 200A and 200B are further described. A PDN level or layer, such as metal layer M5 in the above example, located between upper and lower layers of a plurality of metal layers, such as BEOL metalization upper and lower levels, as previously described, may be coupled to TSVs through corresponding portions of chimney structures, as previously described. These portions of chimney structures may be interconnected for electrical conductivity to one or more TSVs.

For example, current can flow through a TSV 221 of semiconductor die 212 to a partial chimney 239 to a substrate 234 via lower metalization levels 238, as generally indicated by arrow 240. In semiconductor die 233, a PDN layer M5 of such semiconductor die 233 interconnected to substrate 234 through lower metalization and ILD levels 238 may be coupled to such a TSV 221 through portions of upper metalization and ILD levels 239. Upper metalization and ILD levels 239 may be used for formation of a chimney as well as other electrically conductive routing of a semiconductor die 233. Continuing the example of in-flowing current or power to microelectronic device 200B of FIG. 2-2, power may be received via a TSV 221 to a partial chimney 237. A chimney 227 interconnected to TSV 221 of semiconductor die 212 may be coupled for electrical conductivity to a circuit platform 215 to receive such supplied power. In this example, a chimney 217 and TSV 222, the latter of which is interconnected to chimney 227, may be used for supplying power through semiconductor die 211 for semiconductor die 212 and semiconductor die 233. Along those lines, PDN layers M5 of semiconductor dies 211 and 212 may be used to respectively provide power down to substrates 213 and 214, respectively, via lower metalization levels 218 and 228, as generally respectively indicated by arrows 231 and 232.

However, current for a ground interconnection may for example flow from a substrate 234 to a partial chimney 237 via lower metalization levels 238, as generally indicated by arrow 240, in semiconductor die 233. In semiconductor die 233, a PDN layer M5 of such semiconductor die 233 interconnected to substrate 234 through lower metalization and ILD levels 238 may be coupled to a TSV 221 through portions of upper metalization and ILD levels 239, as these upper metalization and ILD levels 239 may be used for formation of a partial chimney 237 as well as other electrically conductive routing of a semiconductor die 233. Continuing the example of supplying a ground for microelectronic device 200B of FIG. 2-2, out-flowing current may be received via a partial chimney 237 to a TSV 221 of semiconductor die 212.

A chimney 227 interconnected to TSV 221 of semiconductor die 212 may be coupled for electrical conductivity to TSV 222 of semiconductor die 211. A chimney 217 interconnected for electrical conductivity to TSV 222 and a circuit platform 215 may be used to pass out-flowing current to such circuit platform. In this example, a chain of chimney 217, TSV 222, chimney 227, TSV 221, partial chimney 237, which are interconnected to one another, may be used for passing current via lower metalization levels 238 from semiconductor die 233 to and through semiconductor dies 212 and 211 for a ground connection of circuit platform 215. Along those lines, PDN layers M5 of semiconductor die 211 and 212 may be used to respectively pass current from substrates 213 and 214 via lower metalization levels 218 and 228, as generally respectively indicated by arrows 231 and 232, to corresponding chimney structures as previously described for output to a ground connection of circuit platform 215.

In order to pass current up or down through a die stack, resistance ("R") is to be reduced from that used in conventional routing. For purposes of clarity by way of example and not limitation, assuming a semiconductor die having 13 metalization levels with a PDN layer M5, it has been observed that resistance through a chimney stack ("stack resistance") from metalization level M13 to M5 may be in a range from greater than 2 and less than 10 ohms, such as 3.5 ohms for example, and resistance through a chimney stack from metalization level M5 to M1 may be equal to or less than 1 ohm. In other words, it has been observed that stack portions of lower metalization layers may be configured to collectively have a stack resistance of equal to or less than 1 ohm from the lowermost metal layer to a PDN layer of a semiconductor die.

The amount of routing congestion between metalization levels M5 and M1 for purposes of a chimney stack may be less than between metalization levels M13 and M5. This allows a chimney stack to have more conductive vias formed for interconnection of metalization levels from a substrate to M1 and up to a PDN layer, namely M5 in this example. The higher density of conductive vias in lower metalization levels in a chimney stack allows for lower stack resistance than in upper metalization levels of such a chimney stack.

Along those lines, a chimney stack may have fewer conductive vias formed for interconnection of metalization levels from a PDN layer, namely M5 in this example, up to the uppermost metalization level due to an increased amount of routing congestion in metalization levels above a PDN layer. For example, horizontal interconnects of upper metalization layers may cross through areas where a TSV area intersects a chimney stack area. Additionally, horizontal interconnects of upper metalization levels may be narrow to provide area for feedthroughs. By bypassing upper metalization levels not part of a chimney stack for distribution of power and ground, higher resistances associated with such upper metalization levels may be avoided.

For purposes of clarity by way of example and not limitation, portions of upper metalization layers associated with a chimney stack may be configured to collectively have a lower stack resistance. In an example, upper metalization layers in a chimney stack were observed to have a resistivity in a range of greater than 2 and less than 10 ohms from the uppermost metal layer to a PDN layer. Additionally, for purposes of clarity by way of example and not limitation, a PDN layer may be configured to have a lowered resistivity. In an example, a PDN layer was observed to have a resistivity of less than 30 ohms for a horizontal trace length of at least 30 microns. By comparison to a conventional 13 metalization level semiconductor die, using an intermediate metalization level for a PDN layer of a 13 metalization level semiconductor die may result in at least a 20 percent reduction in IR drop. While such a configuration may incur no area penalty, a thicker intermediate metalization layer is used to provide a PDN layer which may result in a slightly overall taller semiconductor die. Along those lines, for purposes of clarity by way of example and not limitation, height H1 of an intermediated PDN layer in a BEOL stack as described herein may be at least approximately twice as tall or high with respect to other horizontal traces in such stack. Moreover, a height H1 of an intermediate PDN layer in a BEOL stack as described herein may be at least approximately twice as tall or high as a same metalization level in a conventional chimney stack.

Figures 1, 3:
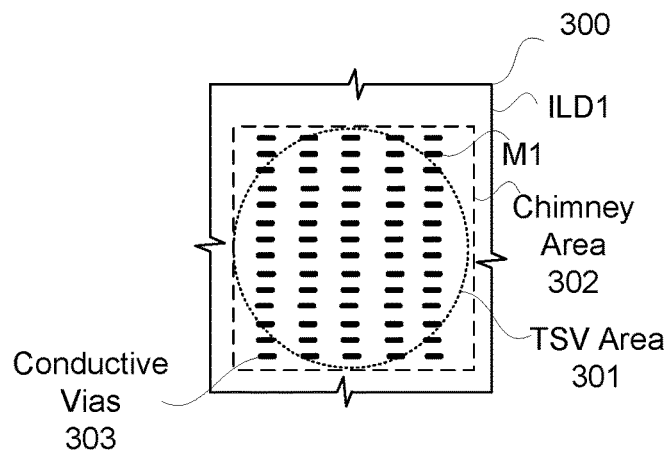
Figures 2, 3:
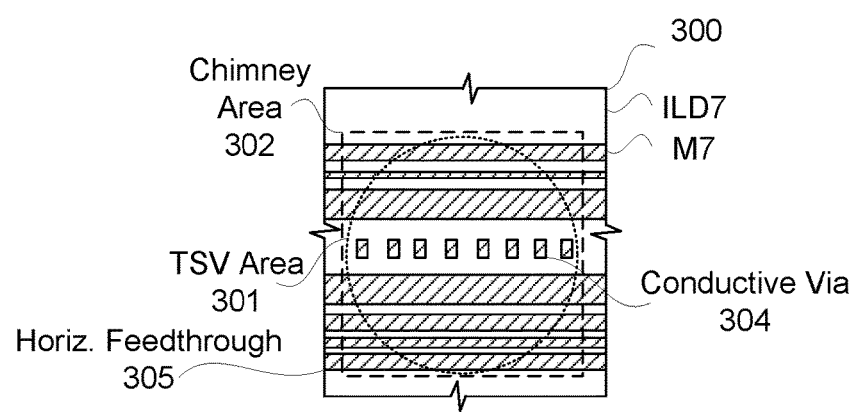
Figure 3:
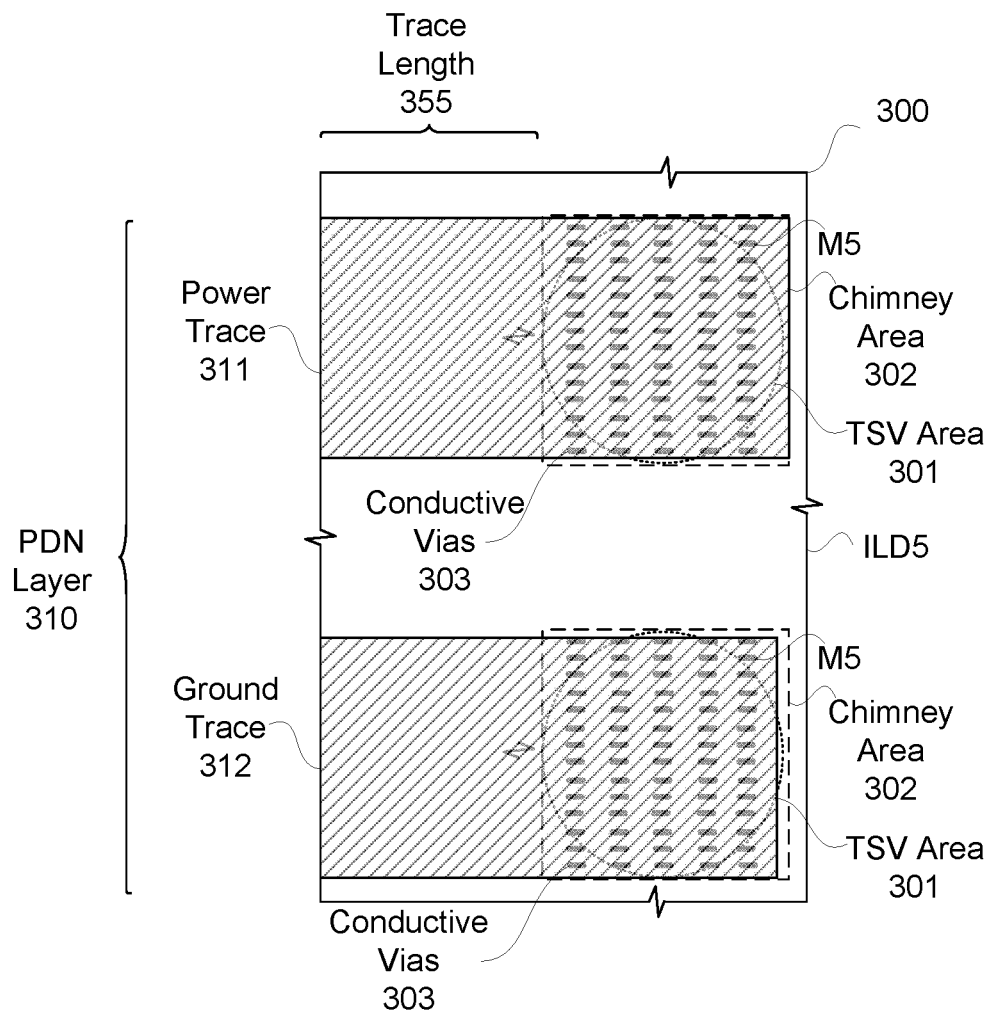

FIG. 3-1 is a block diagram depicting a top-down cross-sectional view of an exemplary portion of a semiconductor die 300 at a lower metalization level. FIG. 3-2 is a block diagram depicting a top-down cross-sectional view of an exemplary portion of a semiconductor die 300 at an upper metalization level. With simultaneous reference to FIGS. 2-1 through 3-2, semiconductor die 300 is further described.

Semiconductor die 300 may be a semiconductor die 211 or 212. The cross-sectional view depicted in FIG. 3-1 is for an example portion of metalization level M1 and ILD level ILD1, though other levels below a PDN level of a BEOL stack may be used. The cross-sectional view depicted in FIG. 3-2 is for an example portion of metalization level M7 and ILD level ILD7, though other levels above a PDN level of a BEOL stack may be used.

Metalization level M1 and ILD level ILD1 may be used for forming a plurality of conductive vias 303 within a chimney area 302. Chimney area 302 may be for a chimney 217 or 227, as previously described. Chimney area 302 may completely overlap a corresponding TSV area 301. TSV area 301 may be of either or both a semiconductor die having conductive vias 303 or an immediately neighboring semiconductor die interconnected to a chimney of such semiconductor die having conductive vias 303.

Metalization level M7 and ILD level ILD7 may be used for forming a plurality of conductive vias 304 within a chimney area 302. Conductive vias 304, though they may have a larger cross-sectional area than conductive vias 303, may be substantially fewer in number within a chimney area 302. Presence of feedthroughs, such as horizontal feedthroughs 305, passing through chimney area 302 limit the amount of area available for conductive vias 304 in such an area. As previously described, routing congestion at metalization levels above an intermediate PDN level may be greater than at metalization levels below such an intermediate PDN level.

Even though cross-sectional area of a conductive via above an intermediate PDN level may be greater than cross-sectional area of a conductive via below such an intermediate PDN level, the number of conductive vias 303 below such an intermediate PDN level within a chimney area 302 may be substantially greater than the number of conductive vias 305 above such an intermediate PDN level within such a chimney area 302 by a factor of at least 2×, and in some instances at least 4×. Accordingly, chimney stack resistance for lower metalization levels may be ⅓ or less that of a chimney stack resistance for upper metalization levels.

FIG. 3-3 is a block diagram depicting a cross-sectional view of an exemplary portion of a semiconductor die 300 at an intermediate PDN level. With simultaneous reference to FIGS. 2-1 through 3-3, semiconductor die 300 is further described.

Again, semiconductor die 300 may be a semiconductor die 211 or 212. The cross-sectional view depicted in FIG. 3-3 is for an example portion of metalization level M5 and ILD level ILD5, though another intermediate metal layer may be used as a PDN level of a BEOL stack. Even though it is assumed that a BEOL stack includes a single intermediate level used to provide a PDN level for purposes of clarity by way of non-limiting example, in other examples more than one intermediate PDN level may be used in a BEOL stack.

Metalization level M5 and ILD level ILD5 may be used for forming a plurality of conductive vias 303 within a chimney area 302, as previously described with reference to FIG. 3-1. Conductive vias 303 may be formed in an ILD5. Trenches may be formed in an ILD5, including above such conductive vias 303 of a metalization layer M5. For a metalization or metal layer M5, such ILD5 formed trenches may be subjected to plating or other deposition of one or more layers, which may include one or more layers of a conductive material, conventionally a metal or mix of metals, for a metal layer M5. Such metal layer M5 in such trenches interconnected to conductive vias 303 may be used to provide conductive traces, such as for example conductive power trace 311 and conductive ground trace 312 of a PDN layer 310. Such in-die power and ground routed bussing provided with traces 311 and 312 of a PDN layer 310 may be thicker than conventional power and ground routing to reduce resistivity, such as for example at least twice as thick as an immediately neighboring upper metal horizontal trace. Along those lines, a PDN layer, such as metal layer M5 for example, may be configured to have a lower resistivity. In an example, a PDN metal layer M5 was observed to have a resistivity of less than 30 ohms for a horizontal trace length 355 of at least 30 microns extension away from a chimney stack structure or region.

Figures 1, 4:
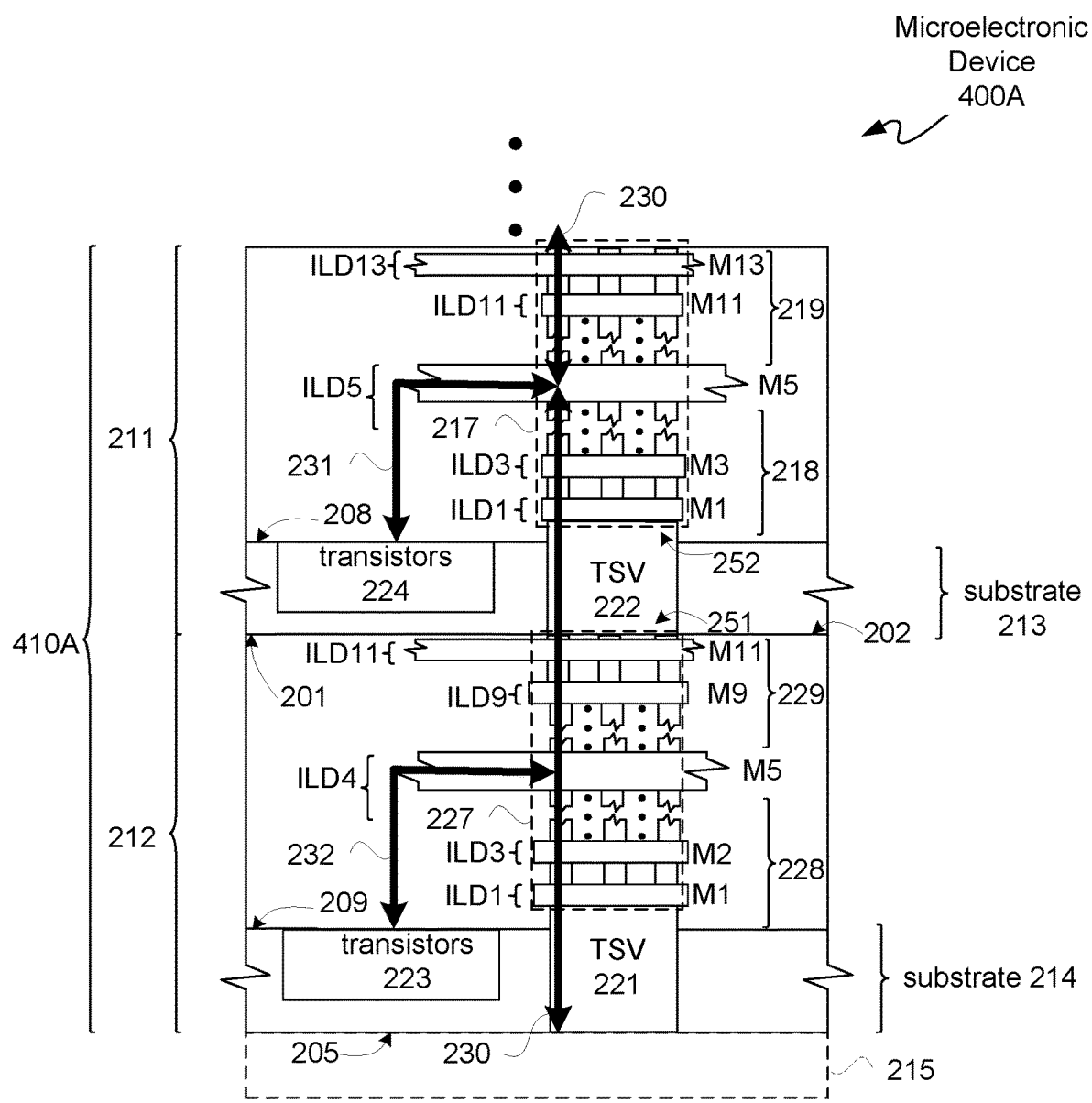
Figures 2, 4:
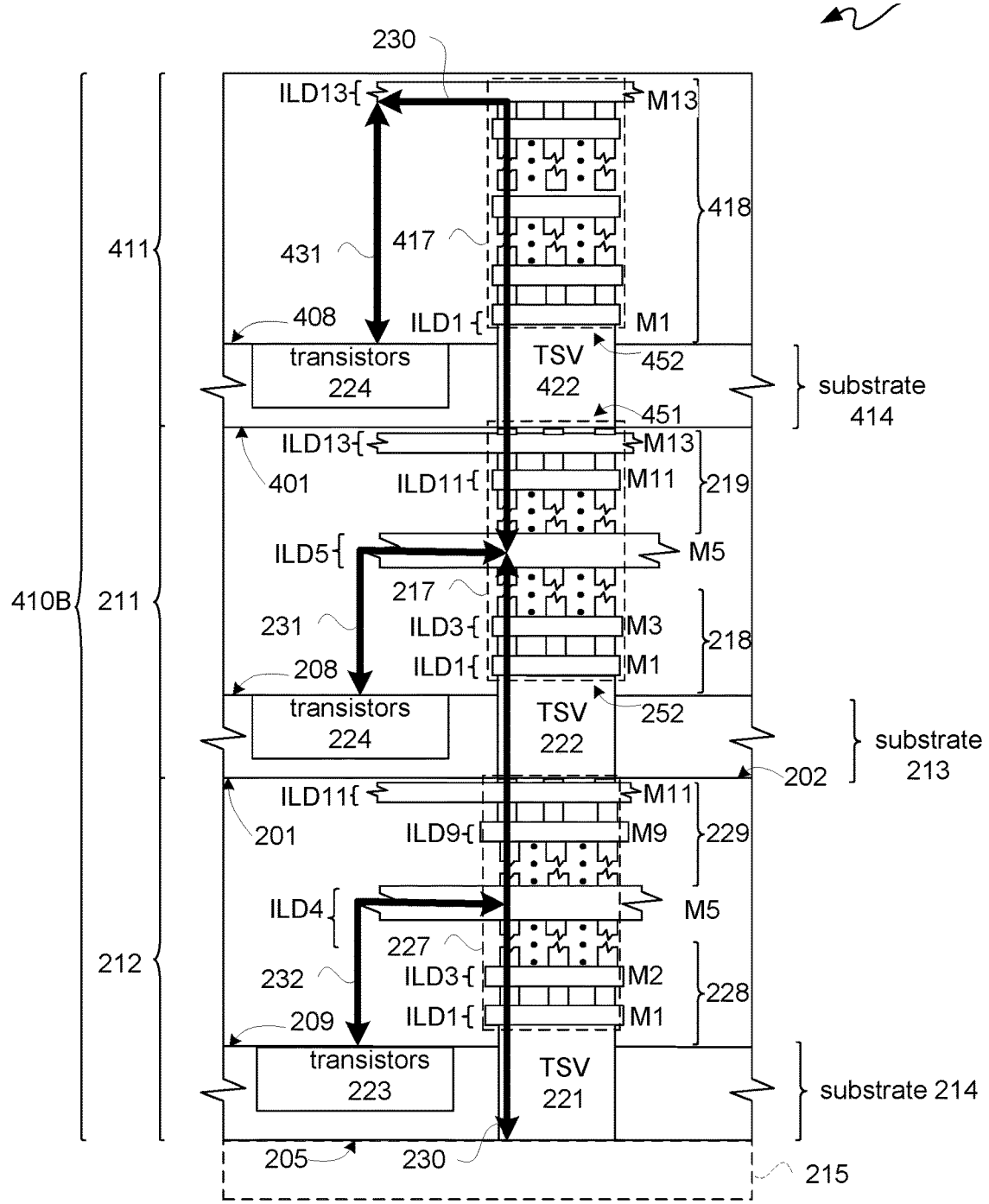

FIG. 4-1 is a block diagram depicting a side view of an exemplary portion of a microelectronic device 400A having a die stack 410A. Die stack 410A includes at least semiconductor dies 211 and 212 as in die stack 210A, as previously described and such description is not repeated for purposes of clarity and not limitation. However, circuit platform 215 is not directly interconnected to a front-side or upper surface of semiconductor die 211 in this example. Rather, a circuit platform 215 in microelectronic device 400A is interconnected to a back-side or lower surface 205 of substrate 214 of lowermost semiconductor die 212 of die stack 410A. Along those lines, a lower end surface of TSV 221 may be interconnected for electrical conductivity to one or more contacts (not shown for purposes of clarity and not limitation) of circuit platform 215. An upper end surface of TSV 221 may be interconnected to a metalization level M1 of lower metalization levels 228 of semiconductor die 212.

Because lower metalization levels 228 and 218 have less chimney stack resistance than upper metalization levels 229 and 219 for corresponding chimneys 227 and 217, current flow, as generally indicated with arrows 230, 231 and 232, may experience less resistance with a reverse die stack orientation, such as in die stack 410A for example, with respect to power and/or ground routed bussing. For example, resistance to a PDN layer M5 by way of TSV 221 and lower metalization layers 228 may be smaller than resistance to PDN layer M5 by way of TSV 222 and upper metalization layers 229. While the uppermost semiconductor die, such as for example semiconductor die 211 in a reverse die stack 410A, may be exposed to any additional resistance of a difference between sets of upper metalization layers 219 and 229, as well as additional resistance of TSVs 221 and 222, than sets of lower metalization layers 228 and 218, and metalization layer M5, such additional resistance may be small compared to resistance for a conductive path to metalization layer M5 of semiconductor die 212 in a die stack 210A of FIG. 2-1.

FIG. 4-2 is a block diagram depicting a side view of an exemplary portion of a microelectronic device 400B having a die stack 410B. Microelectronic device 400B is the same as microelectronic device 400A, except the uppermost semiconductor die 411 on semiconductor die 211 of die stack 410B is a conventional semiconductor die 411. Along those lines, a conventional BEOL stack 418 with a conventional chimney 417 above an upper surface 408 of a substrate 414 and corresponding TSV 422 extending between upper surface 408 and lower surface 401 of substrate 414 may be used. An upper end 452 of TSV 422 may be interconnected to a lowermost metal layer of chimney 417 for electrical conductivity. Furthermore, power and ground are distributed from the uppermost metalization layer, such as an M13 metal layer of a BEOL stack 418, down to substrate 414 of semiconductor die 411, as generally indicated with arrows 230 and 431. A lower end 451 of TSV 422 may be interconnected to the uppermost metal layer, such as metal layer M13, of chimney 217 for electrical conductivity.

Semiconductor dies 211, 212, and/or 414 may be from a same family of integrated circuits. Such as a same family of system-on-chip ("SoC") dies. An example of a SoC die may be a Field Programmable Gate Array or FPGA die. One or more of semiconductor dies 211, 212, and/or 414 may be from different families of integrated circuit dies. Such as a different family of system-on-chip ("SoC") dies. One or more of semiconductor dies 211, 212, and/or 414 may be different types of integrated circuit dies with respect to one another. For example, one of semiconductor dies 211, 212, or 414 may be a memory die, another of semiconductor dies 211, 212, or 414 may be an SoC die, and another of semiconductor dies 211, 212, or 414 may be a focal plane array or other sensor die.

Figure 5:
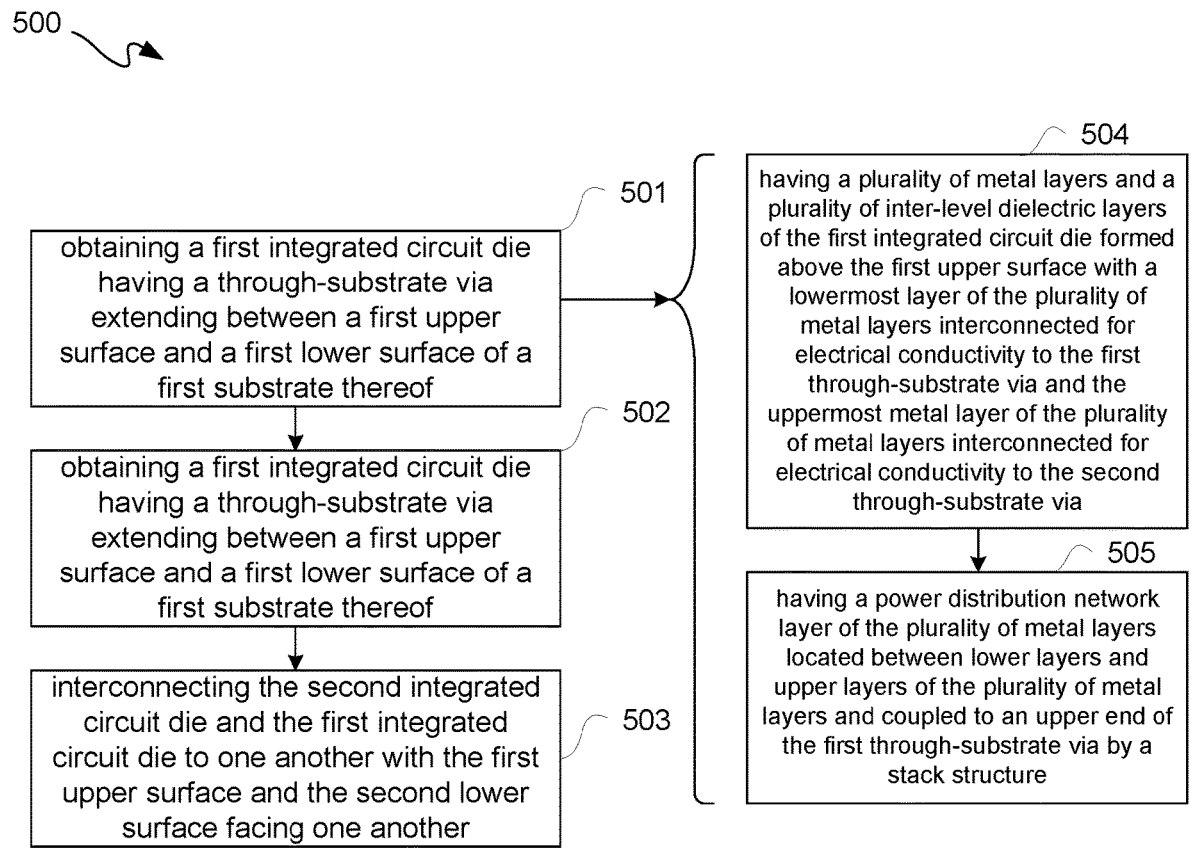
FIG. 5 is a flow diagram depicting an exemplary microelectronic device formation flow.

FIG. 5 is a flow diagram depicting an exemplary microelectronic device formation flow 500. Flow 500 may be for forming a microelectronic device as previously described with reference to FIGS. 1 through 4-2. Accordingly, flow 500 is further described with simultaneous reference to FIGS. 1 through 5.

At 501, a first integrated circuit die having a through-substrate via extending between a first upper surface and a first lower surface of a first substrate thereof may be obtained. Such first integrated circuit die may be in a wafer, such as described with reference to FIG. 1 for WLP, or may be a singulated semiconductor die, such as semiconductor die 212 with TSV 221 for example.

At 502, a second integrated circuit die having a second substrate with a second upper surface and a second lower surface may be obtained. Such second integrated circuit die may be in a wafer, such as described with reference to FIG. 1 for WLP, or may be a singulated semiconductor die, such as semiconductor die 211 with TSV 222 for example.

At 503, such first and second integrated circuit dies may be interconnected to one another with such first upper surface and such second lower surface facing one another. This interconnection may be for die-to-die electrical conductivity. Additionally, this interconnection may include a mechanical interconnection, which may include interconnection for die-to-die electrical conductivity, as well as a dielectric adhesive, a polyimide, or other bonding dielectric layer or layers for die-to-die bonding, such as of bonding semiconductor dies 211 and 212 together.

Obtaining of such first integrated circuit die at operation 501 may include operations 504 and 505. At operation 504, a plurality of metal layers and a plurality of inter-level dielectric layers, respectively such as M1-M11 and ILD1-ILD11 for example, of such first integrated circuit die may be formed or have been formed above such first upper surface with the lowermost layer, such as M1 for example, of such plurality of metal layers interconnected for electrical conductivity to such first through-substrate via and the uppermost layer, such as M11 for example, of such plurality of metal layers interconnected for electrical conductivity to such second through-substrate via.

At operation 505, a power distribution network layer, such as M5 for example, of such plurality of metal layers may be located or have been located between lower layers and upper layers of such plurality of metal layers and coupled to an upper end of such first through-substrate via by a stack structure, such as a lower portion or including a lower portion of chimney 227, namely a partial chimney, formed with lower metalization and ILD levels, as previously described. Such stack structure may include portions of such lower layers including a portion of such lowermost layer interconnected to such upper end of such first through-substrate via.

Again, portions of such lower layers of such stack structure may be configured to collectively have a reduced stack resistance. In an example, a stack resistance of equal to or less than 1 ohm from such lowermost layer to such power distribution network layer was observed. Such power distribution network layer may be configured to have a lowered resistivity. In an example, a power distribution network layer having a resistivity of less than 30 ohms for a horizontal trace length of at least 30 microns was observed. Such power distribution network layer may be at least twice as tall as an immediately neighboring metal layer of such upper layers of such plurality of metal layers with respect to horizontal traces respectively thereof.

Because one or more of the examples described herein may be implemented in an FPGA, a detailed description of such an IC is provided. However, it should be understood that other types of ICs may benefit from the technology described herein.

Programmable logic devices ("PLDs") are a well-known type of integrated circuit that can be programmed to perform specified logic functions. One type of PLD, the field programmable gate array ("FPGA"), typically includes an array of programmable tiles. These programmable tiles can include, for example, input/output blocks ("IOBs"), configurable logic blocks ("CLBs"), dedicated random access memory blocks ("BRAMs"), multipliers, digital signal processing blocks ("DSPs"), processors, clock managers, delay lock loops ("DLLs"), and so forth. As used herein, "include" and "including" mean including without limitation.

Each programmable tile typically includes both programmable interconnect and programmable logic. The programmable interconnect typically includes a large number of interconnect lines of varying lengths interconnected by programmable interconnect points ("PIPs"). The programmable logic implements the logic of a user design using programmable elements that can include, for example, function generators, registers, arithmetic logic, and so forth.

The programmable interconnect and programmable logic are typically programmed by loading a stream of configuration data into internal configuration memory cells that define how the programmable elements are configured. The configuration data can be read from memory (e.g., from an external PROM) or written into the FPGA by an external device. The collective states of the individual memory cells then determine the function of the FPGA.

Another type of PLD is the Complex Programmable Logic Device, or CPLD. A CPLD includes two or more "function blocks" connected together and to input/output ("I/O") resources by an interconnect switch matrix. Each function block of the CPLD includes a two-level AND/OR structure similar to those used in Programmable Logic Arrays ("PLAs") and Programmable Array Logic ("PAL") devices. In CPLDs, configuration data is typically stored on-chip in non-volatile memory. In some CPLDs, configuration data is stored on-chip in non-volatile memory, then downloaded to volatile memory as part of an initial configuration (programming) sequence.

For all of these programmable logic devices ("PLDs"), the functionality of the device is controlled by data bits provided to the device for that purpose. The data bits can be stored in volatile memory (e.g., static memory cells, as in FPGAs and some CPLDs), in non-volatile memory (e.g., FLASH memory, as in some CPLDs), or in any other type of memory cell.

Other PLDs are programmed by applying a processing layer, such as a metal layer, that programmably interconnects the various elements on the device. These PLDs are known as mask programmable devices. PLDs can also be implemented in other ways, e.g., using fuse or antifuse technology. The terms "PLD" and "programmable logic device" include but are not limited to these exemplary devices, as well as encompassing devices that are only partially programmable. For example, one type of PLD includes a combination of hard-coded transistor logic and a programmable switch fabric that programmably interconnects the hard-coded transistor logic.

Figure 6:
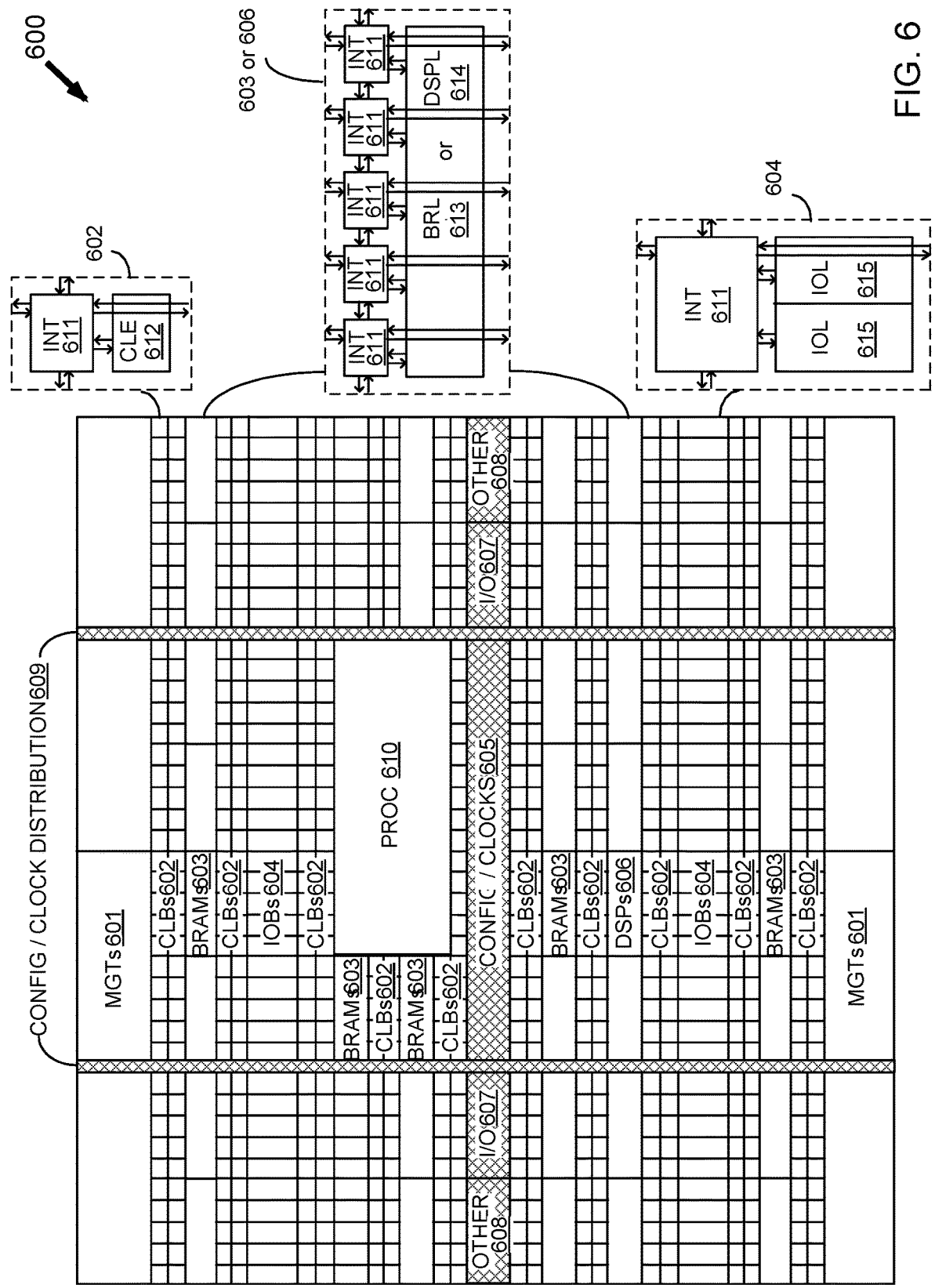
FIG. 6 is a simplified block diagram depicting an exemplary columnar Field Programmable Gate Array ("FPGA") architecture.

As noted above, advanced FPGAs can include several different types of programmable logic blocks in the array. For example, FIG. 6 illustrates an FPGA architecture 600 that includes a large number of different programmable tiles including multi-gigabit transceivers ("MGTs") 601, configurable logic blocks ("CLBs") 602, random access memory blocks ("BRAMs") 603, input/output blocks ("IOBs") 604, configuration and clocking logic ("CONFIG/CLOCKS") 605, digital signal processing blocks ("DSPs") 606, specialized input/output blocks ("I/O") 607 (e.g., configuration ports and clock ports), and other programmable logic 608 such as digital clock managers, analog-to-digital converters, system monitoring logic, and so forth. Some FPGAs also include dedicated processor blocks ("PROC") 610.

In some FPGAs, each programmable tile includes a programmable interconnect element ("INT") 611 having standardized connections to and from a corresponding interconnect element in each adjacent tile. Therefore, the programmable interconnect elements taken together implement the programmable interconnect structure for the illustrated FPGA. The programmable interconnect element 611 also includes the connections to and from the programmable logic element within the same tile, as shown by the examples included at the top of FIG. 6.

For example, a CLB 602 can include a configurable logic element ("CLE") 612 that can be programmed to implement user logic plus a single programmable interconnect element ("INT") 611. A BRAM 603 can include a BRAM logic element ("BRL") 613 in addition to one or more programmable interconnect elements. Typically, the number of interconnect elements included in a tile depends on the height of the tile. In the pictured embodiment, a BRAM tile has the same height as five CLBs, but other numbers (e.g., four) can also be used. A DSP tile 606 can include a DSP logic element ("DSPL") 614 in addition to an appropriate number of programmable interconnect elements. An 10B 604 can include, for example, two instances of an input/output logic element ("IOL") 615 in addition to one instance of the programmable interconnect element 611. As will be clear to those of skill in the art, the actual I/O pads connected, for example, to the I/O logic element 615 typically are not confined to the area of the input/output logic element 615.

In the pictured embodiment, a horizontal area near the center of the die (shown in FIG. 6) is used for configuration, clock, and other control logic. Vertical columns 609 extending from this horizontal area or column are used to distribute the clocks and configuration signals across the breadth of the FPGA.

Some FPGAs utilizing the architecture illustrated in FIG. 6 include additional logic blocks that disrupt the regular columnar structure making up a large part of the FPGA. The additional logic blocks can be programmable blocks and/or dedicated logic. For example, processor block 610 spans several columns of CLBs and BRAMs.

Note that FIG. 6 is intended to illustrate only an exemplary FPGA architecture. For example, the numbers of logic blocks in a row, the relative width of the rows, the number and order of rows, the types of logic blocks included in the rows, the relative sizes of the logic blocks, and the interconnect/logic implementations included at the top of FIG. 6 are purely exemplary. For example, in an actual FPGA more than one adjacent row of CLBs is typically included wherever the CLBs appear, to facilitate the efficient implementation of user logic, but the number of adjacent CLB rows varies with the overall size of the FPGA.

While the foregoing describes exemplary apparatus(es) and/or method(s), other and further examples in accordance with the one or more aspects described herein may be devised without departing from the scope hereof, which is determined by the claims that follow and equivalents thereof. Claims listing steps do not imply any order of the steps. Trademarks are the property of their respective owners.

What is claimed is:

1. A method for forming an active-on-active microelectronic device, comprising:
   obtaining a first die having a first substrate with a through-substrate via extending between a top surface and a bottom surface of the first substrate;
   obtaining a second die having a second substrate with a top surface and a bottom surface;
   interconnecting the first die on the second die with the bottom surface of the first substrate facing the top surface of the second substrate to provide a die stack;
   wherein the first die and the second die each have a plurality of metal layers formed in a plurality of inter-level dielectric layers to provide a first stack structure and a second stack structure, respectively, for electrical conductivity;
   wherein the first stack structure is interconnected to an upper end of the through-substrate via for electrical conductivity;

the interconnecting including connecting a metal layer of the second stack structure near the bottom surface of the first substrate for electrical conductivity to a lower end of the through-substrate via;
wherein a power distribution network layer of the second stack structure is located between lower layers and upper layers of the plurality of metal layers thereof;
wherein a first transistor and a second transistor are respectively located at least in part in the first substrate and the second substrate; and
wherein the second transistor is interconnected to the power distribution network layer to receive at least one of a supply voltage or a ground.

2. The method according to claim 1, further comprising:
wherein the through-substrate via is a first through-substrate via;
wherein the second die has a second through-substrate via extending between the top surface and the bottom surface of the second substrate;
wherein a third die has a third substrate with a top surface and a bottom surface;
wherein the third die has a plurality of metal layers formed in a plurality of inter-level dielectric layers to provide a third stack structure for electrical conductivity; and
interconnecting the second die on the third die with the bottom surface of the second substrate facing the top surface of the third substrate to provide the die stack.

3. The method according to claim 2, wherein:
the second stack structure is interconnected to an upper end of the second through-substrate via for electrical conductivity; and
the interconnection of the second die on the third die includes connecting a metal layer of the third stack structure near the bottom surface of the second substrate interconnected for electrical conductivity to a lower end of the second through-substrate via.

4. The method according to claim 3, wherein:
the power distribution network layer is a first power distribution network layer;
the first stack structure has a second power distribution network layer located between lower layers and upper layers of the plurality of metal layers thereof;
the third stack structure has a third power distribution network layer located between lower layers and upper layers of the plurality of metal layers thereof;
the first transistor of the first die is interconnected to the second power distribution network layer to receive the at least one of the supply voltage or the ground; and
a third transistor of the third die is interconnected to the third power distribution network layer to receive the at least one of the supply voltage or the ground.

5. A method for forming an active-on-active microelectronic device, comprising:
obtaining a first die comprising a first substrate with a top surface and a bottom surface, and a first plurality of metal layers comprising metal layers alternatingly extending in a direction away from the first substrate;
obtaining a second die comprising a second substrate with a through-substrate via extending between a top surface and a bottom surface of the second substrate; and
interconnecting the first die with the second die to provide a die stack by connecting the first plurality of metal layers to the though-substrate via,
wherein the first plurality of metal layers comprises:
a first metal layer closest to the first substrate;
a second metal layer farthest from the first substrate; and
a first power distribution network layer configured to provide at least one of a supply voltage or ground to a first standard cell of the first die, and disposed above the first metal layer and below the second metal layer, and wherein the first power distribution network layer is thicker than the first metal layer and the second metal layer.

6. The method of claim 5, wherein the first power distribution network layer is at least twice as thick as the first metal layer and the second metal layer.

7. The method of claim 5, the first power distribution network layer has a lower resistivity relative to each of the first plurality of metal layers disposed above the first power distribution network layer and each of the first plurality of metal layers disposed below the first power distribution network layer.

8. The method of claim 5, wherein the second die further comprises a second plurality of metal layers, the second plurality of metal layers comprises:
a third metal layer closest to the second substrate;
a fourth metal layer farthest from the second substrate; and
a second power distribution network layer disposed above the third metal layer and below the fourth metal layer, and wherein the second power distribution network layer is thicker than the third metal layer and the fourth metal layer.

9. The method of claim 8, the second power distribution network layer has a lower resistivity relative to each of second first plurality of metal layers disposed above the second power distribution network layer and each of the second plurality of metal layers disposed below the second power distribution network layer.

10. The method of claim 8 further comprising:
obtaining a third die comprising a third substrate with a second through-substrate via extending between a top surface and a bottom surface of the third substrate; and
interconnecting the second die with the third die by connecting the second plurality of metal layers to the second though-substrate via.

11. The method of claim 10, wherein the third die further comprises a third plurality of metal layers, the third plurality of metal layers comprises:
a fifth metal layer closest to the third substrate;
a sixth metal layer farthest from the third substrate; and
a third power distribution network layer disposed above the fifth metal layer and below the sixth metal layer.

12. The method of claim 10, wherein connecting the second plurality of metal layers to the second though-substrate via comprises connecting the fourth metal layer to the second through-substrate via.

13. The method of claim 5, wherein connecting the first plurality of metal layers to the though-substrate via comprises connecting the second metal layer to the through-substrate via.

14. A method for forming an active-on-active microelectronic device, comprising:
obtaining a first die comprising a first plurality of metal layers formed in a first plurality of inter-level dielectric layers to provide a first stack structure;
obtaining a second die having a standard cell formed therein and a second plurality of metal layers disposed on the standard cell to provide a second stack structure; and interconnecting the first die with the second die to provide a die stack by bonding the first die with the second die at a bonding interface, wherein the second stack structure comprises a first power distribution network layer located between a first metal layer of the second plurality of metal layers closest to the standard cell and a last metal layer of the second plurality of metal layers farthest from the standard cell, the first power distribution network layer configured to provide at least one of a supply voltage or ground to the standard cell, wherein the first power distribution network layer is thicker than the first metal layer and the last metal layer.

15. The method of claim 14, wherein bonding the first die with the second die comprises coupling a first through-substrate via with a second through-substrate via, wherein the first through-substrate via extends between a top surface to a bottom surface of a first substrate of the first die, and the second through-substrate via extends between a top surface and a bottom surface of a second substrate of the second die.

16. The method of claim 14 further comprising:

obtaining a third die having a third plurality of metal layers formed in a third plurality of inter-level dielectric layers to provide a third stack structure for electrical conductivity; and interconnecting the second die with the third die.

17. The method of claim 14, wherein the first power distribution network layer has a lower resistivity relative to the second plurality of metal layers.

18. The method of claim 14, wherein the first power distribution network layer has a thickness that is at least twice as thick as a metal layer of the second plurality of metal layers disposed above the standard cell.

19. The method of claim 14, wherein:

upper layers of the second plurality of metal layers are configured to have a stack resistance of greater than 2 but less than 10 ohms, the upper layers disposed above the first power distribution network layer; and lower layers of the second plurality of metal layers are configured to have a stack resistance of equal to or less than 1 ohm, the lower layers disposed between the standard cell and the first power distribution network layer.

20. The method of claim 19, wherein the second stack structure is configured to have a higher via density in the lower layers than in the upper layers to provide a lower resistivity path through the lower layers than the upper layers.

* * * * *